United States Patent
Knauthe et al.

(10) Patent No.: US 6,677,324 B1
(45) Date of Patent: Jan. 13, 2004

(54) COMBINATION PREPARATION OF ESTROGEN AND ANTI-ESTROGEN

(75) Inventors: Rudolf Knauthe, Berlin (DE); Christa Hegele-Hartung, Berlin (DE)

(73) Assignee: Schering Aktiengesellschaft, Berlin (DE)

( * ) Notice: Subject to any disclaimer, the term of this patent is extended or adjusted under 35 U.S.C. 154(b) by 0 days.

(21) Appl. No.: 09/622,532

(22) PCT Filed: Feb. 18, 1999

(86) PCT No.: PCT/EP99/01023

§ 371 (c)(1),
(2), (4) Date: Aug. 21, 2000

(87) PCT Pub. No.: WO99/42109

PCT Pub. Date: Aug. 26, 1999

(30) Foreign Application Priority Data

Feb. 19, 1998 (DE) .......................... 198 07 791

(51) Int. Cl.⁷ ................................. A61K 31/56
(52) U.S. Cl. ..................................... 514/170
(58) Field of Search ......................... 514/170

(56) References Cited

U.S. PATENT DOCUMENTS 5,145,847 A    9/1992   Yukishige et al.
5,866,560 A  * 2/1999   Bohlmann et al. .......... 514/182

FOREIGN PATENT DOCUMENTS

DE   19622457   11/1997
EP    0138504    4/1985
EP    0346014  * 12/1989
WO    9807740    2/1998

* cited by examiner

Primary Examiner—Barbara P. Badio
(74) Attorney, Agent, or Firm—Millen, White, Zelano & Branigan, P.C.

(57) ABSTRACT

The invention describes a combination preparation of an oestrogen and an antioestrogen, characterized in that the oestrogen is selected from the group consisting of 17-β-oestradiol, 17-α-ethynyloestradiol, oestriol, oestrone, oestrone sulphate, oestrogen sulphamates, 17α-oestradiol, mestranol, stilboestrol and naturally conjugated oestrogens and in that the antioestrogen is a substituted 7α-(ξ-aminoalkyl)oestratriene of the general formula I

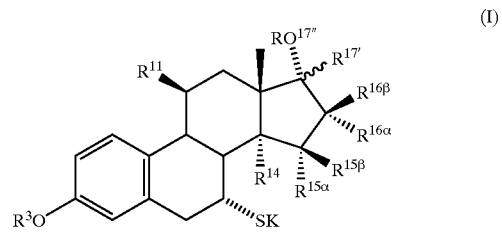

The combination preparation according to the invention can be used for hormone substitution therapy.

18 Claims, 4 Drawing Sheets

COMBINATION PREPARATION OF ESTROGEN AND ANTI-ESTROGEN

This application is a 371 of FCT/EP99/01023 filed Feb. 18, 1999.

The invention relates to a combination preparation of an oestrogen and an antioestrogen. Owing to the decreasing production of oestrogen, during the change of life and after the menopause acute symptoms needing treatment, such as hot flushes, suddenly occurring outbreaks of sweating, racing heart and other vasomotor symptoms occur in many women. The loss of the endogenous oestrogens can lead in the long term to an increased loss of bone mass (osteoporosis) and to an increase in cardiovascular disorders. More recent epidemiological investigations have shown that physiological and pathological ageing symptoms of the central nervous system are partially to be attributed to the loss of oestrogen. Examples of these which may be mentioned are limitations of the memory power of the short-term memory (S. M. Phillips, B. B. Sherwin, 1992, Psychoneuroendocrinology 17, 485) and Alzheimer's disease (A. Paganini-Hill, V. W. Henderson, 1994, Am. J. Epidemiol. 140, 256).

Hormone replacement therapy has the aim of substituting the losses of the endogenous oestrogens commencing with the menopause and thus preventing both the acute and the long-term symptoms. Today the therapy is either carried out as oestrogen monotherapy or as combination therapy with gestagens. A disadvantage of the monotherapy is the proliferative action of the oestrogen on the endometrium, which can lead to endometrial hyperplasia and adenocarcinomas. With combination therapy, withdrawal bleeding or intracyclic menstrual bleeding occurs, which markedly restricts the acceptance of the therapy and frequently leads to the discontinuance of the therapy. Furthermore, adverse effects of the gestagens on the cardioprotective and positive central actions of the oestrogens are discussed.

A further possibility for hormone substitution is the combination of an oestrogen with an antioestrogen. In this case, the protective effects of the oestrogen in the bone should be retained, while the undesired effects on the endometrium should be antagonized (EP 0346014). It is, however, disadvantageous when the antioestrogen reaches the central nervous system and antagonizes the positive properties of oestrogen there. It is reported, for example, for tamoxifen that it induces typical, acute climacteric symptoms such as hot flushes (S. Litherland, M. Jackson, 1987, Cancer Treat Revs. 15, 183). It. was possible to show that the substance reaches the central nervous system and acts there as an oestroaenic antagonist (A. Biegon et al., 1996, Cancer Research 56, 4328). It would also not be desirable if the antioestrogen were to counteract the protective action of the oestrogen in Alzheimer's disease.

The technical problem then lies in finding a combination preparation of an oestrogen and an antioestrogen in which the antioestrogenic component does not reach the central nervous system and simultaneously has an antiproliferative action on the endometrium.

The problem is now solved in that a combination preparation has been found in which the oestrogen is selected from the group consisting of 17-β-oestradiol, 17-α-ethynyloestradiol, oestriol, oestrone, oestrone sulphate, oestrogen sulphamates, 17α-oestradiol, mestranol, stilboestrol, esters of 17β-oestradiol, such as, for example, oestradiol valerate and naturally conjugated oestrogens and in that the antioestrogen is a substituted 7α-(ξ-aminoalkyl) oestratriene of the general formula I (I)

in which
the side chain SK is a radical of the subformula

—(CH$_2$)$_{\overline{m}}$—N—CH—CH—(CH$_2$)$_{\overline{n}}$—SO$_{\overline{x}}$—(CH$_2$)$_3$—E
　　　　　　　|　　|　　|
　　　　　　　A　　B　　D where m is 4, 5 or 6,
n is 0, 1 or 2,
x is 0, 1 or 2,
A is a hydrogen atom or a C$_{1-5}$-alkyl group,
B and D are each a hydrogen atom, or
A and B together are an alkylene group —(CH$_2$)$_p$— with p=2, 3, 4 or 5 and D is a hydrogen atom or
A and D together are an alkylene group —(CH$_2$)$_q$— with q=2, 3 or 4 and B is a hydrogen atom, and
E is an unsubstituted or mono- to pentafluorinated ethyl radical, or the terminal substituent —(CH$_2$)$_3$—E in the side chain is replaced by an optionally substituted aryl or heteroaryl radical which is bonded to the sulphur atoms directly or via a mono-, di- or trimethylene group,
R$^3$ is a hydrogen atom, a hydrocarbon radical having up to 8 carbon atoms or a radical of the subformula R$^{3'}$—C(O)—, in which R is a hydrogen atom or a hydrocarbon radical having up to 8 carbon atoms or a phenyl radical,
R$^{11}$ is a hydrogen atom, a halogen atom or a nitrooxy group —O—NO$_2$,
R$^{14}$, R$^{15\alpha}$, R$^{15\beta}$, R$^{16\alpha}$ and R$^{16\beta}$ are each a hydrogen atom or
R$^{14}$ and R15α are an additional bond or a methylene bridge, or
R$^{15\beta}$ is a methyl group and R$^{15\alpha}$ is a hydrogen atom, or
R$^{15\alpha}$ and R$^{15\beta}$ are each a methyl group, or
R$^{15\beta}$ and R$^{16\beta}$ together are a methylene bridge, or
R$^{16\alpha}$ or R$^{16\beta}$ is a halogen atom or
R$^{16\alpha}$ and R$^{16\beta}$ together are a methylidene group and the remaining substituents R$^{14}$, R$^{15\alpha}$, R$^{15\beta}$, R$^{16\alpha}$ and R$^{16\beta}$ are each a hydrogen atom,
R$^{17'}$ in the α- or β-position is a hydrogen atom, a C$_{1-5}$-alkyl, C$_{2-5}$-alkenyl or C$_{2-5}$-alkynyl group or a trifluoromethyl group and
R$^{17''}$ is a hydrogen atom or a radical of the subformula R$^{17'''}$—C(O)—, in which R$^{17'''}$ is a hydrogen atom or a hydrocarbon radical having up to 8 carbon atoms, or, if R$^{17'}$ is located in the α-position, R$^{17'}$ together with R$^{14}$ is an ethano bridge,
with the proviso that, if A and B together are not —(CH$_2$)$_p$— or A and D together are not —(CH$_2$)$_q$—, at least one of: the substituents R$^{11}$, R$^{14}$, R$^{15\alpha}$, R$^{15\beta}$, R$^{16\alpha}$ and R$^{16\beta}$ and R$^{16\beta}$ is not a hydrogen atom,
and their physiologically tolerable addition salts with organic and inorganic acids.

Moreover, a combination preparation is made available in which the oestrogen is selected from the group consisting of 17-β-oestradiol, 17-α-ethynyloestradiol, oestriol, oestrone, oestrone sulphate, oestrogen sulphamates, 17α-oestradiol, mestranol, stilboestrol, esters of 17β-oestradiol, such as, for example, oestradiol valerate and natural conjugated oestrogens and the antioestrogen is an 11β-halo-7α-substituted oestratriene of the general formula II (II)

in which
R$^3$ is a hydrogen atom, a hydrocarbon radical having up to 8 carbon atoms or a radical of the subformula R$^{3'}$—C(O)—, in which R$^{3'}$ is a hydrogen atom or a hydrocarbon radical having up to 8 carbon atoms or a phenyl radical,
R$^7$ is a radical of the formula —A—B—Z—R$^{20}$, in which
A is a direct bond or a benzylidene radical, where the methylene group is bonded to the 7-carbon atom of the steroid, or a phenylene radical,
B is a straight- or branched-chain alkylene, alkenylene or alkynylene group having 3 to 14 carbon atoms, and
Z is —NR$^{21}$— and R$^{21}$ is a C$_1$–C$_3$-alkyl group, where R$^{20}$ then is
  a hydrogen atom,
  a straight- or branched-chain alkyl, alkenyl or alkynyl group having up to 10 carbon atoms, or one of the groups
  —D—C$_n$F$_{2n-1}$, where D is a straight- or branched-chain alkylene, alkenylene or alkynylene group having up to 8 carbon atoms and n is an integer from 1 to 8,
  —L—CH=CF—C$_p$F$_{2p+1}$, where L is a straight- or branched-chain alkylene, alkenylene or alkynylene group having 2 to 7 carbon atoms and p is an integer from 2 to 7,
  —D—O—(CH$_2$)$_q$-aryl, where D has the meaning already indicated, q is 0, 1, 2 or 3 and aryl is an optionally mono- or disubstituted phenyl radical, 1- or 2-naphthyl radical or a heteroaryl radical,
  —D—O—(CH$_2$)$_r$—C$_n$F$_{2n+1}$, where D and n have the meanings already indicated and r is an integer from 1 to 5, or
  R$^{20}$ and R$^{21}$ with the nitrogen atom to which they are bonded form a saturated or unsaturated heterocycle having 5 or 6 chain members, which optionally contains one or two further heteroatoms selected from nitrogen, oxygen and sulphur, and is optionally substituted, or
Z is —SO$_x$— and x is 0, 1 or 2, where R$^{20}$ then is
  a straight- or branched-chain alkyl, alkenyl or alkynyl group having up to 10 carbon atoms, or one of the groups
  —D—C$_n$F$_{2n+1}$, where D is a straight- or branched-chain alkylene, alkenylene or alkynylene group having up to 8 carbon atoms and n is an integer from 1 to 8,
  —L—CH=CF—C$_p$F$_{2p+1}$, where L is a straight- or branched-chain alkylene, alkenylene or alkynylene group having 2 to 7 carbon atoms and p is an integer from 2 to 7,
  —D—O—(CH$_2$)$_q$-aryl, where D has the meaning already indicated, q is 0, 1, 2 or 3 and aryl is an optionally mono- or disubstituted phenyl radical, 1- or 2-naphthyl radical or a heteroaryl radical,
  —D—O—(CH$_2$)$_r$—C$_n$F$_{2n+1}$, where D and n have the meanings already indicated and r is an integer from 1 to 5, or
Z is —NR$^{31}$—,
  where R$^{20}$ then is a straight- or branched-chain alkyl, alkenyl or alkynyl radical having up to 14 carbon atoms, which can be interrupted by one to three heteroatoms —O— and —S— and groups —NR$^{32}$—, in which R$^{32}$ is a hydrogen atom or a C$_1$–C$_3$-alkyl radical, and/or can be partially fluorinated, an optionally mono- or disubstituted aryl or heteroaryl radical, an optionally mono- or disubstituted C$_3$–C$_{10}$-cycloalkyl radical, an optionally mono- or disubstituted C$_4$–C$_{15}$-cycloalkylalkyl radical, an optionally mono- or disubstituted C$_7$–C$_{20}$-aralkyl radical, an optionally mono- or disubstituted heteroaryl-C$_{1-C6}$-alkyl radical or an optionally substituted aminoalkyl radical, and
  R$^{31}$ is a radical of the formula —C(O)R$^{33}$ or —CH$_2$—R$^{33}$,
  where R$^{33}$ then is a straight- or branched-chain alkyl, alkenyl or alkynyl radical having up to 14 carbon atoms, which can be interrupted by one to three heteroatoms —O— and —S— and groups —NR$^{32}$—, in which R$^{32}$ is a hydrogen atom or a C$_1$–C$_3$-alkyl radical, and/or can be partially fluorinated, an optionally mono- or disubstituted aryl or heteroaryl radical, an optionally mono- or disubstituted C$_3$–C$_{10}$-cycloalkyl radical, an optionally mono- or disubstituted C$_4$–C$_{15}$-cycloalkylalkyl radical, an optionally mono- or disubstituted C$_7$–C$_{20}$-aralkyl radical, an optionally mono- or disubstituted heteroaryl-C$_1$–C$_6$-alkyl radical, an optionally substituted aminoalkyl radical or a biphenylene radical,
excluding the compounds
  11β-fluoro-7α-{5-[N-methyl-N-3-(4,4,5,5,5-pentafluoropentylthio)propylamino]pentyl}oestra-1,3,5(10-triene-3,17β-diol
  7α-{5-[(2S)-2-(4,4,5,5,5-pentafluoropentylthiomethyl)-pyrrolidin-1-yl]pentyl}oestra-1,3,5(10)-triene-3,17β-diol
  7α-{5-[(2R)-2-(4,4,5,5,5-pentafluoropentylthiomethyl)-pyrrolidin-1-yl]pentyl}oestra-1,3,5(10)-triene-3,17β-diol
  11β-fluoro-7α-{5-[2-(4,4,5,5,5-pentafluoropentylthioethyl)pyrrolidin-1-yl]pentyl}oestra-1,3,5(10)-triene-3,17β-diol
  11β-fluoro-7α-{5-[N-methyl-N-3-(4,4,5,5,5-pentafluoropentylthio)propylamino]pentyl}-3-hydroxyoestra-1,3,5(10)-trien-17-one
  11β-fluoro-7α-{6-[N-methyl-N-3-(4,4,5,5,5-pentafluoropentylthio)propylamino]hexyl}oestra-1,3,5(10)-triene-3,17β-diol
  11β-fluoro-7α-{5-[(2S)-2-(4-trifluoromethylphenylthiomethyl)pyrrolidin-1-yl]pentyl}oestra-1,3,5(10)-triene-3,17β-diol 11β-fluoro-7α-{5-[(2S)-2-(4,4,5,5,5-pentafluoropentyl-thiomethyl)pyrrolidin-1-yl]pentyl}oestra-1,3,5(10)-triene-3,17β-diol 11β-fluoro-7α-{5-[(2S)-2-(4,4,5,5,5-pentafluoropentane-sulphinylmethyl)pyrrolidin-1-yl]pentyl}oestra-1,3,5(10)-triene-3,17β-diol 11β-fluoro-7α-{5-[(2S)-2-(4,4,5,5,5-pentafluoropentane-sulphonylmethyl)pyrrolidin-1-yl]pentyl}oestra-1,3,5(10)-triene-3,17β-diol $R^{11}$ is a fluorine or chlorine atom, $R^{17}$ is a hydrogen atom or a radical of the subformula $R^{17'}$—C(O)—, in which $R^{17'}$ is a hydrogen atom or a hydrocarbon radical having up to 8 carbon atoms.

Combination preparation means that the oestrogen and the antioestrogen are made available in one pharmaceutical package in the same administration form or in different administration forms and are administered either simultaneously or successively. Antioestrogen means a substance which has no or only very low oestrogenic activity, binds to the oestrogen receptor and prevents the action of the oestrogen. An antioestrogen counteracts the increase in the uterus weight and/or the increase in the uterus epithelial depth in spayed female rats or mice which have been substituted with oestradiol benzoate. The sole treatment of spayed rats with the antioestrogen does not lead to the stimulation (increase) of the uterus weight or of the epithelial depth in comparison to untreated animals.

The compounds of the general formula I and II have a very strong antioestrogenic action and do not pass into the central nervous system. They are therefore particularly suitable for combining with an oestrogen, since they do not inhibit the positive properties of the oestrogen in the brain.

The ratio of the dose of the oestrogen to the dose of the antioestrogen is 1:5 to 1:100, preferably 1:20 to 1:200, most preferably 1:50 to 1:100.

The combination of an oestrogen with the antioestrogen 11β-fluoro-7α-{5-[N-methyl-N-3-(4,4,5,5,5-pentafluoro-pentylthio)propylamino]pentyl}oestra-1,3,5(10)-triene-3,17β-diol is preferred.

The combination of an oestrogen with an antioestrogen which is selected from the group consisting of 11β-fluoro-7α-{5-[methyl-(8,8,9,9,9-pentafluoro-nonyl)amino]pentyl}oestra-1,3,5(10)-triene-3,17β-diol 11β-fluoro-7α-{6-[methyl—(8,8,9,9,9-pentafluoro-nonyl)aminolhexyl}oestra-1,3,5(10)-triene-3,17β-diol 11β-fluoro-7α-{5-[methyl-(7,7,8,8,9,9,10,10,10-nonafluorodecyl)amino]pentyl}oestra-1,3,5(10)-triene-3,17β-diol 11β-fluoro-7α-{5-[methylnonylamino]pentyl}oestra-1,3,5(10)-triene-3,17β-diol 11β-fluoro-7α-{5-[3,4,4,5,5,5-hexafluoropent-2-enyl)methylamino]pentyl}oestra-1,3,5(10)-triene-3,17β-diol 11β-fluoro-7α-{5-[N-methyl-N-3-(4,4,5,5,5-penta-fluoropentyloxy)propylamino]pentyl}oestra-1,3,5(10)-triene-3,17β-diol 4-biphenyl-N-[6-(11β-fluoro-3,17β-dihydroxyoestra-1,3,5(10)-trien-7α-yl)hexyl]-N-(3-phenylpropyl)-acetamide is additionally preferred.

The antioestrogen can be administered orally, transdermally, as an implant or intravenously. The oestrogen can be administered orally, transdermally, intravenously or as an implant. All possible combinations of the administration forms for oestrogen and antioestrogen are possible here.

The invention furthermore relates to the use of the combination preparation according to the invention for the production of a medicament for male and female hormone substitution therapy. This can be used for the prevention and therapy of post-menopausal osteoporosis, in the case of climacteric symptoms and in Alzheimer's disease. Further indications are the therapy of hot flushes, of depressive conditions due to the change of life, improvement in cognition, cardiovascular protection and therapy, immunoprotection, the therapy of symptoms as a result of dysmenorrhoea, of dysfunctional uterine haemorrhages, acne, restenosis, hypercholesterolaemia and of hyperlipidaemia, the prevention and treatment of arteriosclerosis, the prevention of loss of bone mass in women who have had a hysterectomy or in women who have been treated with LHRH agonists or antagonists, the treatment of endometriosis and myomas in combination with LHRH analogues and the inhibition of the proliferation of the arterial smooth muscle cells.

The invention further relates to pharmaceutical agents or compositions which contain the combination preparation according to the invention, if appropriate together with the formulating substances and additives customary in pharmacy.

FIGURES

FIG. 1

FIG. 2

FIG. 3

FIG. 4

The following examples serve to illustrate the invention in greater detail:

EXAMPLE 1

Synthesis of 11β-Fluoro-7α-{5-EN-methyl-N-3-(4,4,5,5,5-pentafluoropentylthio)propylamino]pentyl}-oestra-1,3,5(10)-triene-3,17β-diol a) 11β-Fluorooestr-4-ene-3,17-dione 4.6 ml of perfluorobutane-1-sulphonyl fluoride are added dropwise at 0° C. to 5.0 g of 11β-hydroxyoestr-4-ene-3,17-dione in 100 ml of toluene and 7.3 ml of 1,8-diazabicyclo[5.4.0]undec-7-ene. After 30 min, the solution is diluted with ethyl acetate, washed with saturated sodium chloride solution, dried and concentrated in vacuo. After chromatographing the crude product on silica gel using a hexane-ethyl acetate gradient, 3.8 g of 11β-fluorooestr-4-ene-3,17-dione of melting point 173–174° C. are obtained.

b) 11β-Fluoro-3-methoxyoestra-3,5-dien-17-one 7.8 g of 11β-fluorooestr-4-ene-3,17-dione are stirred at 80° C. for 5 h with 780 mg of pyridinium toluene-4-sulphonate in 40 ml of 2,2-dimethoxypropane. 1.5 ml of triethylamine are then added, and the mixture is diluted with ethyl acetate and washed with saturated sodium chloride solution. After crystallization from methanol, 5.3 g of 11β-fluoro-3-methoxyoestra-3,5-dien-17-one of melting point 173° C. are obtained.

c) 11β-Fluorooestra-4,6-diene-3,17-dione 5 ml of a 10% sodium acetate solution and, in portions, 2.5 g of 1,3-dibromo-5,5-dimethylhydantoin are added successively at 0° C. to 5.0 g of 11β-fluoro-3-methoxy-oestra-5-dien-3,17-one in 50 ml of DMF. After 30 min, 2.3 g of sodium sulphite and then 2.5 g of lithium bromide and 2.0 g of lithium carbonate are added, and the mixture is stirred at 100° C. for 2 h. The reaction mixture is stirred into ice-water. The precipitated product is filtered off with suction, dissolved in ethyl acetate, and the solution is washed with water, dried and concentrated in vacuo. After recrystallization from ethyl acetate, 3.6 g of 11β-flouorooestra-4,6-diene-3,17-dione of melting point 198° C. are obtained.

d) 11β-Fluoro-7α-(5-tert-butyldimethylsilyloxy-pentyl)oestr-4-ene-3,17-dione 7.9 g of magnesium in 40 ml of THF are reacted under nitrogen with a solution of 95.3 g of 1-bromo-5-tert-butyldimethylsilyloxypentane [Tetrahedron Letters 1982, 4147–4150] in 260 ml of THF to give the Grignard reagent. 32 g of copper(I) iodide are added at −30° C. and then, dropwise, 29 g of 11β-flouorooestra-4,6-diene-3,17-dione in 290 ml of THF. After reaction is complete, the reaction mixture is treated with 20.4 ml of glacial acetic acid and stirred into ice-water. The precipitated product is filtered off with suction, dissolved in ethyl acetate, and the solution is washed with water until neutral and dried. After chromatographing the crude product on silica gel using a hexane-ethyl acetate gradient, 23.9 g of 11β-fluoro-7α-(5-tert-butyldimethylsilyloxypentyl)oestr-4-ene-3,17-dione are obtained as a foam.

e) 11β-Fluoro-7α-(5-hydroxypentyl)oestr-4-ene-3,17-dione

A solution of 23.1 g of 11β-fluoro-7α-(5-tert-butyl-dimethylsilyloxypentyl)oestr-4-ene-3,17-dione in 115 ml of THF and 64 ml of water are stirred at 50° C. for 2.5 h with 128 ml of glacial acetic acid. The reaction mixture is concentrated in vacuo, taken up in ethyl acetate, and the solution is washed with water and dried. 20.4 g of 11β-fluoro-7α-(5-hydroxypentyl)oestr-4-ene-3,17-dione are obtained as a foam.

f) 7α-(5-Acetoxypentyl)-11β-fluorooestr-4-ene-3,17-dione 20 g of 11β-fluoro-7α-(5-hydroxypentyl)oestr-4-ene-3,17-dione in 100 ml of pyridine are allowed to react at 25° C. for 2 h with 50 ml of acetic anhydride. 5 ml of water are then added at 0° C. and the mixture is stirred for 45 min. It is extracted with diethyl ether, washed with 2N sulphuric acid until free of pyridine and neutralized successively with saturated sodium hydrogencarbonate solution and water. After drying and concentrating in vacuo, the crude product is chromatographed on silica gel using a hexane-ethyl acetate gradient. 17 g of 7α-(5-acetoxypentyl)-11β-fluorooestr-4-ene-3,17-dione of melting point 78.4° C. are obtained.

g) 7α-(5-Acetoxypentyl)-11-fluoro-3-hydroxyoestra-1,3,5(10)-trien-17-one 18.6 g of copper(II) bromide and 3.6 g of lithium bromide are added at 80° C. to 16.5 g of 7α-(5-acetoxy-pentyl)-11β-fluorooestr-4-ene-3,17-dione in 190 ml of acetonitrile. After 15 min, the reaction mixture is stirred into ice-water containing sodium hydrogen-carbonate. The precipitated product is filtered off with suction, dissolved in ethyl acetate, and the solution is washed with water, dried and concentrated in vacuo. After chromatographing the crude product on silica gel using a hexane-ethyl acetate gradient, 8.5 g of 7α-(5-acetoxypentyl)-11β-fluoro-3-hydroxyoestra-1,3,5(10)-trien-17-one are obtained as a foam.

h) 7α-(5-Acetoxypentyl)-11β-fluoro-3-(tetrahydro-pyran-2-yloxy)oestra-1,3,5(10)-trien-17-one 8.2 g of 7α-(5-acetoxypentyl)-11β-fluoro-3-hydroxyestra-1,3,5(10)-trien-17-one in 86 ml of THF are stirred at RT for 2.5 h with 8.6 ml of 3,4-dihydro-2H-pyran and 820 mg of p-toluenesulphonic acid. 0.5 ml of triethylamine is then added, and the mixture is diluted with ethyl acetate, washed with saturated sodium chloride solution, dried and concentrated in vacuo. After chromatographing the crude product on silica gel using a hexane-ethyl acetate gradient, 7.8 g of 7α-(5-acetoxypentyl)-11β-fluoro-3-(tetrahydropyran-2-yloxy) oestra-1,3,5(10)-trien-17-one are obtained as a foam.

i) 11β-Fluoro-7α-(5-hydroxypentyl)-3-(tetrahydro-pyran-2-yloxy)oestra-1,3,5(10)-trien-17-one 7.4 g of 7α-(5-acetoxypentyl)-11β-fluoro-3-(tetrahydropyran-2-yloxy)oestra-1,3,5(10)-trien-17-one are stirred with 1.8 g of potassium carbonate at room temperature in 370 ml of methanol and 37 ml of water. After 3 h, the reaction mixture is added to ice-water. The precipitated product is filtered off with suction, dissolved in ethyl acetate, and the solution is washed with water until neutral, dried and concentrated in vacuo. 7.0 g of 11β-fluoro-7α-(5-hydroxypentyl)-3-(tetrahydropyran-2-yloxy)oestra-1,3,5(10)-trien-17-one are obtained as a foam.

j) 11-Fluoro-3-(tetrahydropyran-2-yloxy)-7α-(5-p-toluenesulphonyloxypentyl)oestra-1,3,5(10)-trien-17-one 6.7 g of 11β-fluoro-7α-(5-hydroxypentyl)-3-(tetrahydropyran-2-yloxy)oestra-1,3,5(10)-trien-17-one in 70 ml of pyridine are stirred with 6.0 g of p-toluenesulphonic anhydride for 3 h at room temperature. The solution is diluted with ethyl acetate, washed with saturated sodium chloride solution, dried and concentrated in vacuo. The crude product is chromatographed on silica gel using a hexane-ethyl acetate gradient. 5.7 g of 11β-fluoro-3-(tetrahydropyran-2-yloxy)-7α-(5-p-toluene-sulphonyloxylpentyl)oestra-1,3,5(10)-trien-17-one are obtained as a foam.

k) 11β-Fluoro-7α-{5-[N-methyl-N-3-(4,4,5,5,5-penta-fluoropentylthio)propylamino]pentyl}-3-(tetrahydro-pyran-2-yloxy)oestra-1,3,5(10)-trien-17-one 2.0 g of 11β-fluoro-3-(tetrahydropyran-2-yloxy)-7α-(5-p-toluenesulphonyloxypentyl)oestra-1,3,5(10)-trien-17-one in 44 ml of DMF are stirred at 80° C. with 1.2 g of methyl-[3-(4,4,5,5,5-pentafluoropentylthio)propyl]-amine. After 6.5 h, the reaction mixture is treated with water. The mixture is extracted with ethyl acetate, washed with saturated sodium chloride solution and concentrated in vacuo. After chromatographing the crude product on silica gel using a methylene chloride-methanol gradient, 1.3 g of 11-fluoro-7α-{5-[N-methyl-N-3-(4,4,5,5,5-pentafluoropentylthio)propylamino]-pentyl}-3-(tetrahydropyran-2-yloxy)oestra-1,3,5(10)-trien-17-one are obtained as an oil.

l) 11β-Fluoro-7α-{5-[N-methyl-N-3-(4,4,5,5,5-penta-fluoropentylthio)propylamino]pentyl}-3-(tetrahydro-pyran-2-yloxy)oestra-1,3,5(10)-trien-17β-ol 350 mg of sodium borohydride are added in portions at 0° C. to 2.0 g of 11β-fluoro-7α-{5-[N-methyl-N-3-(4,4,5,5,5-pentafluoropentylthio)propylamino]pentyl}-3-(tetrahydropyran-2-yloxy)oestra-1,3,5(10)-trien-17-one in 17 ml of THF, 10 ml of ethanol and 4.2 ml of water. After 30 min, the reaction mixture is stirred into ice-water, extracted with ethyl acetate, washed with saturated sodium chloride solution and concentrated in vacuo. 1.7 g of crude 11β-fluoro-7α-{5-[N-methyl-N-3-(4,4,5,5,5-pentafluoropentylthio)propylamino]pentyl}-3-(tetrahydropyran-2-yloxy)oestra-1,3,5(10)-trien-17β-ol are obtained as a foam.

m) 11β-Fluoro-7α-{5-[N-methyl-N-3-(4,4,5,5,5-penta-fluoropentylthio)propylaminolpentyl}oestra-1,3,5(10)-triene-3,17β-diol A solution of 1.6 g of 11β-fluoro-7x-{5-[N-methyl-N-3-(4,4,5,5,5-pentafluoropentylthio)propylamino]pentyl}-3-(tetrahydropyran-2-yloxy)oestra-1,3,5(10)-trien-17β-ol in 20 ml of methanol and 2 ml of water is stirred with 1.0 g of oxalic acid. After 3 h, the reaction mixture is added to ice-water. The mixture is extracted with methylene chloride, washed with saturated sodium chloride solution, dried and concentrated in vacuo. After chromatographing the crude product on silica gel using a methylene chloride-methanol gradient, 1.1 g of 11β-fluoro-7α-{5-[N-methyl-N-3-(4,4,5,5,5-pentafluoro-pentylthio)propylamino]pentyl}oestra-1,3,5(10)-triene-3,17β-diol of melting point 95° C. are obtained.

EXAMPLE 2

Action of the Combination Preparation on Uterus and Bone

The doses of the oestrogen and antioestrogen to be used for the selective bone action test must be established to begin with in preliminary investigations.

The dose of the antioestrogen to be used is determined by an antiuterus growth test in the oestradiol-substituted, ovarectomized rat. The dose to be selected should lower the uterus weight exactly to the level of untreated, ovarectomized female rats.

The oestrogen dose is established by the uterus growth test in the ovarectomized female rats. The dose is selected which brings about m stimulation of the uterus weight in this model which is found in intact comparison animals.

In the combination to be tested, the antioestrogen is administered in the dose defined above. The oestrogen is administered in various combinations with the antioestrogen in a 10-fold lower to 100-fold greater dose, as was established for the particular oestrogen in the uterus growth test.

In the selective bone action test, female ovarectomized rats 3 months old were treated for 28 days with the active compound combinations defined above, the treatment being possible orally, subcutaneously or in a combination of both application routes.

Figure 1:
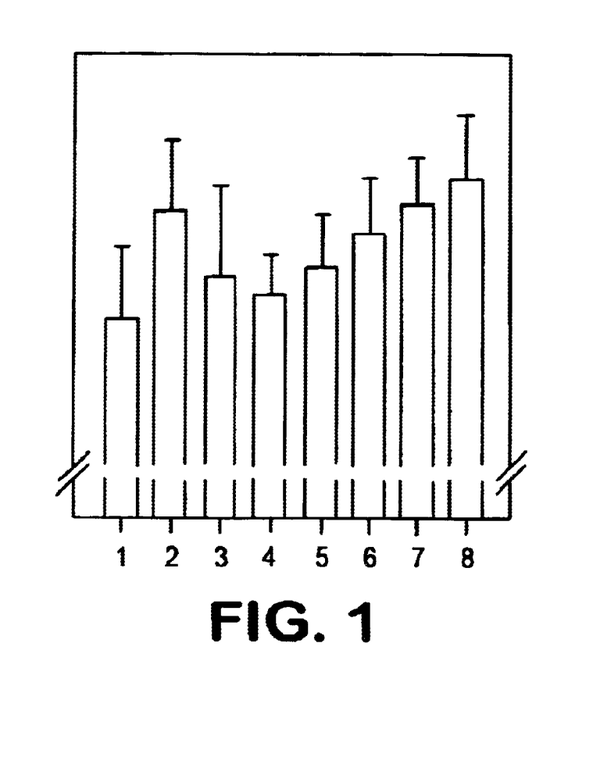
FIG. 1 shows the effect of different combinations of oestradiol and 11β-fluoro-7α-{5-[N-methyl-N-3-(4,4,5,5,5-pentafluoropentylthio)propylamino]pentyl}-oestra-1,3,5(10)-triene-3,17β-diol (=test substance) on the trabecular bone of the proximal tibia of the ovarectomized rat. In the FIG. 1 means: control (only solvent), 2: 0.3 μg of oestradiol, 3: 75 μg of test substance, 4: 75 μg of test substance+0.03 μg of oestradiol, 5: 75 μg of test substance+0.1 μg of oestradiol, 6: 75 μg of test substance+0.3 μg of oestradiol, 7: 75 μg of test substance+1.0 μg of oestradiol, 8: 75 μg of test substance+3.0 μg of oestradiol.
Figure 2:
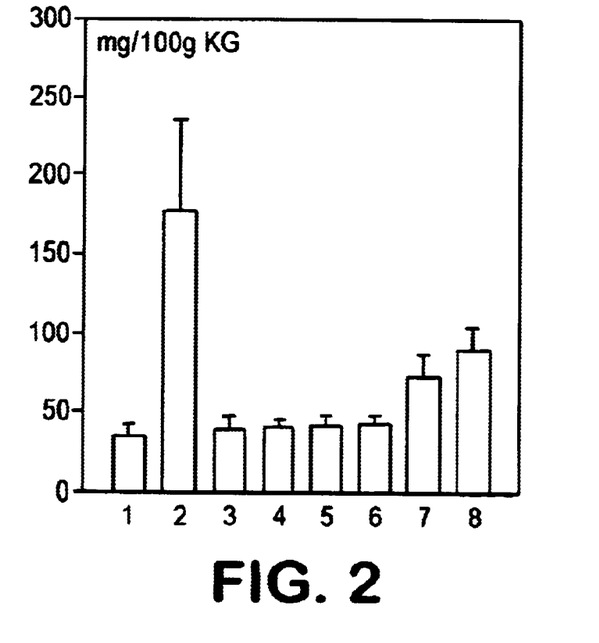
FIG. 2 shows the effect of different combinations of oestradiol and 11β-fluoro-7α-{5-[N-methyl-N-3-(4,4,5,5,5-pentafluoropentylthio)propylamino]pentyl}-oestra-1,3,5(10)-triene-3,17β-diol (=test substance) on the uterus weight of ovarectomized female rats. In the FIG. 1 means: control (only solvent), 2: 0.3 μg of oestradiol, 3: 75 μg of test substance, 4: 75 μg of test substance+0.03 μg of oestradiol, 5: 75 μg of test substance+0.1 μg of oestradiol, 6: 75 μg of test substance+0.3 μg of oestradiol, 7: 75 μg of test substance+1.0 μg of oestradiol, 8: 75 μg of test substance+3.0 μg of oestradiol.
Figure 3:
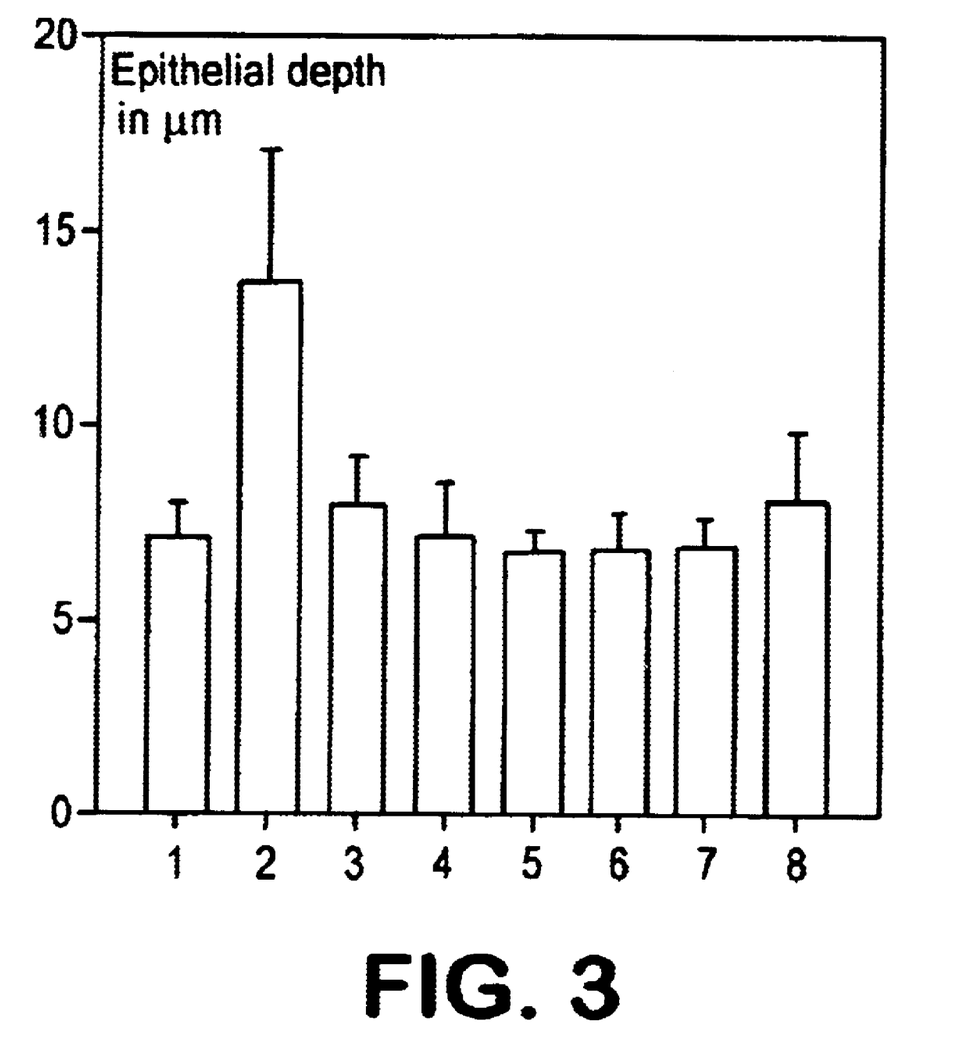
FIG. 3 shows the effect of different combinations of oestradiol and 11β-fluoro-7α-{5-[N-methyl-N-3-(4,4,5,5,5-pentafluoropentylthio)propylamino]pentyl}-oestra-1,3,5(10)-triene-3,17β-diol (=test substance) on the depth of the luminal uterine epithelium. In the FIG. 1 means: control (only solvent), 2: 0.3 μg of oestradibl, 3: 75 μg of test substance, 4: 75 μg of test substance+0.03 μg of oestradiol, 5: 75 μg of test substance+0.1 μg of oestradiol, 6: 75 μg of test substance+0.3 μg of oestradiol, 7: 75 μg of test substance+1.0 μg of oestradiol, 8: 75 μg of test substance+3.0 μg of oestradiol.
Figure 4A:
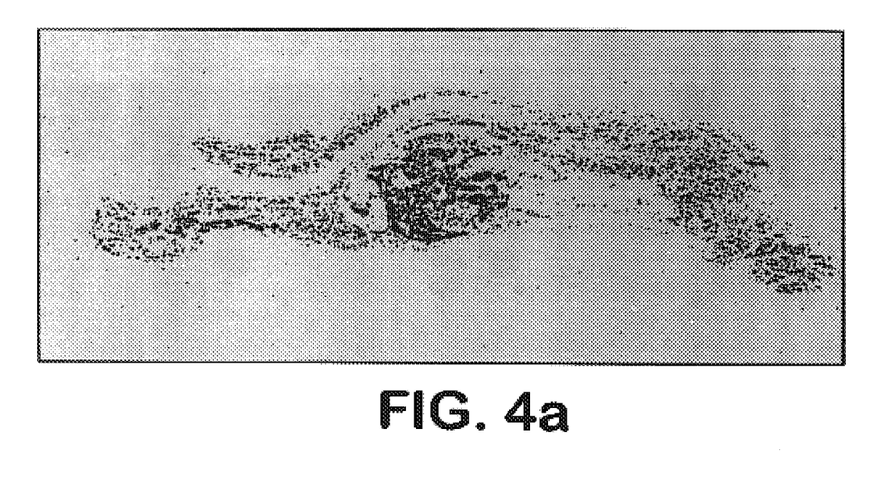
FIG. 4 shows that 11β-fluoro-7α-{5-[N-methyl-N-3-(4,4,5,5,5-pentafluoropentylthio)propylamino]pentyl}-oestra-1,3,5(10)-triene-3,17β-diol does not pass into the central nervous system. Tissue distributions of $^{14}$C-labelled 11β-fluoro-7α-{5-[N-methyl-N-3-(4,4,5,5,5-pentafluoropentylthio)propylamino]pentyl}oestra-1,3,5(10)-triene-3,17β-diol are shown 30 min (a) and 180 min (b) after i.v. administration. For comparison, tissue distributions of 17β-oestradiol are shown 30 min (c) and 180 min (d) after i.v. administration.
Figure 4B:
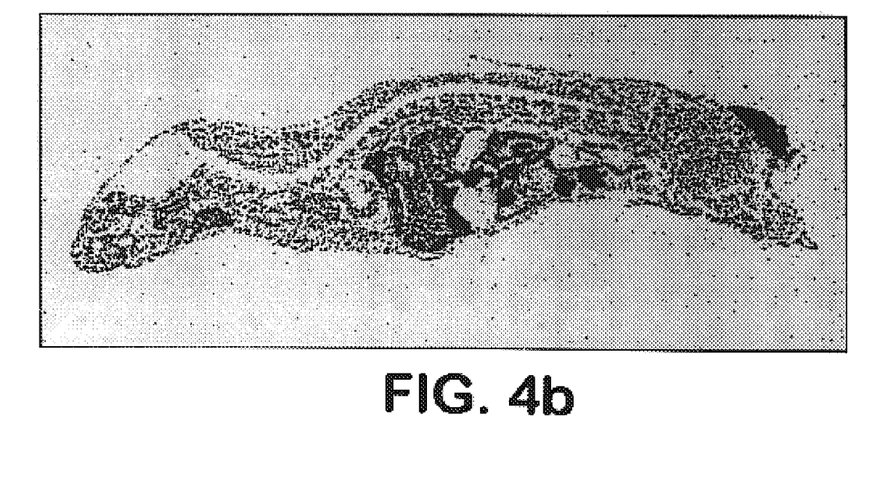
Figure 4C:
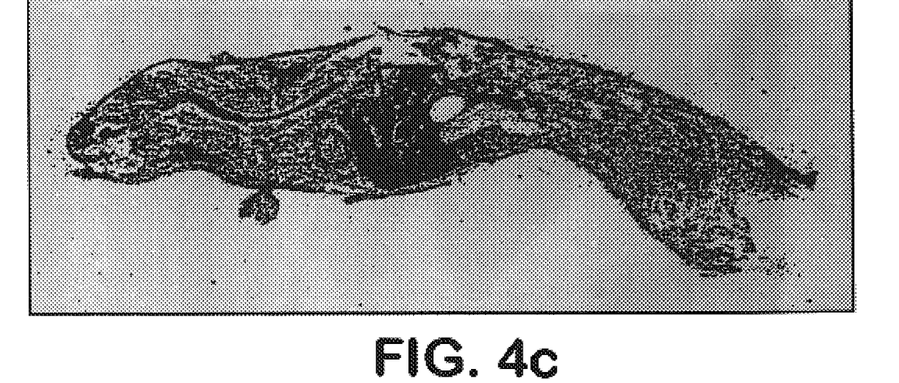
Figure 4D:
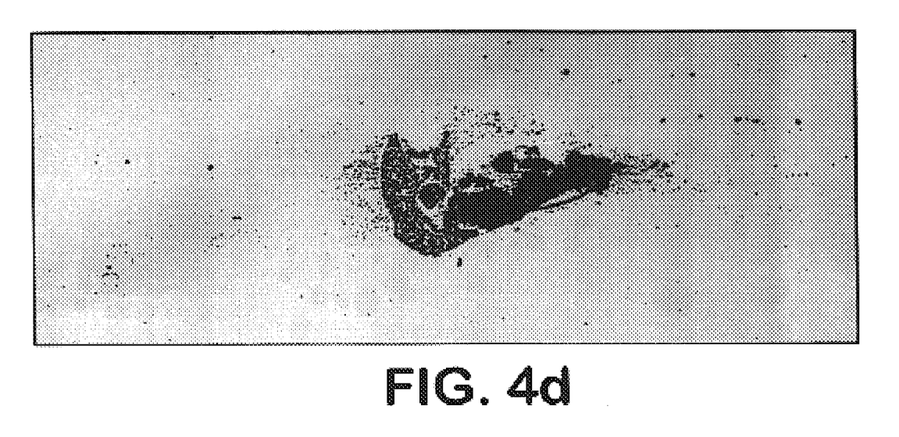

After 28 days, the animals are killed and the uterus weight, as well as the trabecular bone density in the proximal tibia, is measured. The uterus weight is determined by weighing the uterus moist weight immediately after organ removal. The trabecular bone density is determined ex vivo by bone density measurements in the secondary spongiosa of the proximal tibia using a QCT (Stratec XCT 960A). A typical example of a selectively active combination of an oestrogen with an antioestrogen is shown in FIGS. 1–3 for the active compounds 17β-oestradiol and 11β-fluoro-7α-{5-[N-methyl-N-3-(4,4,5,5,5-pentafluoropentylthio)propyl-amino]pentyl}oestra-1,3,5(10)-triene-3,17β-diol (substance from Example 1).

EXAMPLE 3

Demonstration that the Antioestrogen does not Reach the Central Nervous System

Female rats (about 180 g) are treated once with 1 mg/kg of the $^{14}$C-labelled test substance (2 MBq/kg). The test substance is dissolved in propylene glycol/water and administered intravenously. 0.5 and 3.0 hours after administration, one test animal in each case is killed and sagittal whole body sections are prepared. The tissue distribution is determined by whole-body autoradiography. A typical example is shown in FIG. 4 for 11β-fluoro-7α-{5-[N-methyl-N-3-(4,4,5,5,5-penta-fluoropentylthio)propylamino]pentyl}oestra-1,3,5(10)-triene-3,17β-diol (substance from Example 1).

EXAMPLE 4

11β-Fluoro-7α-{5-[methyl-(8,8,9,9,9-pentafluoro-nonyl)amino]pentyl}oestra-1,3,5(10)-triene-3,17β-diol a) 11β-Fluorooestr-4-ene-3,17-dione 4.6 ml of perfluorobutane-1-sulphonyl fluoride are added dropwise at 0° C. to 5.0 g of 11α-hydroxyoestr-4-ene-3,17-dione in 100 ml of toluene and 7.3 ml of 1,8-diazabicyclo [5.4.0]undec-7-ene. After 30 min, the solution is diluted with ethyl acetate, washed with saturated sodium chloride solution, dried and concentrated in vacuo. After chromatographing the crude product on silica gel using a hexane-ethyl acetate gradient, 3.8 g of 11β-fluorooestr-4-ene-3,17-dione of melting point 173–174° C. are obtained.

b) 11β-Fluoro-3-methoxyoestra-3,5-dien-17-one 7.8 g of 11β-fluorooestr-4-ene-3,17-dione are stirred at 80° C. for 5 h with 780 mg of pyridinium toluene-4-sulphonate in 40 ml of 2,2-dimethoxypropane. 1.5 ml of triethylamine are then added, and the mixture is diluted with ethyl acetate and washed with saturated sodium chloride solution. After crystallization from methanol, 5.3 g of 11β-fluoro-3-methoxyoestra-3,5-dien-17-one of melting point 173° C. are obtained.

c) 11β-Fluorooestra-4,6-diene-3,17-dione 5 ml of a 10% sodium acetate solution and, in portions, 2.5 g of 1,3-dibromo-5,5-dimethylhydantoin are added successively at 0° C. to 5.0 g of 11β-fluoro-3-methoxy-oestra-5-dien-3,17-dione in 50 ml of DMF. After 30 min, 2.3 g of sodium sulphite and then 2.5 g of lithium bromide and 2.0 g of lithium carbonate are added, and the mixture is stirred at 100° C. for 2 h. The reaction mixture is stirred into ice-water. The precipitated product is filtered off with suction, dissolved in ethyl acetate, and the solution is washed with water, dried and concentrated in vacuo. After recrystallization from ethyl acetate, 3.6 g of 11-fluorooestra-4,6-diene-3,17-dione of melting point 198° C. are obtained.

d) 11β-Fluoro-7α-(5-tert-butyldimethylsilyloxy-pentyl) oestr-4-ene-3,17-dione 7.9 g of magnesium in 40 ml of THF are reacted under nitrogen with a solution of 95.3 g of 1-bromo-5-tert-butyldimethylsilyloxypentane [Tetrahedron Letters 1982, 4147–4150] in 260 ml of THF to give the Grignard reagent. 32 g of copper(I) iodide are added at −30° C. and then, dropwise, 29 g of 11β-fluorooestra-4,6-diene-3,17-dione in 290 ml of THF. After reaction is complete, the reaction mixture is treated with 20.4 ml of glacial acetic acid and stirred into ice-water. The precipitated product is filtered off with suction, dissolved in ethyl acetate, and the solution is washed with water until neutral and dried. After chromatographing the crude product on silica gel using a hexane-ethyl acetate gradient, 23.9 g of 11β-fluoro-7α-(5-tert-butyldimethylsilyloxypentyl)oestr-4-ene-3,17-dione are obtained as a foam.

e) 11β-Fluoro-7α-(5-hydroxypentyl)oestr-4-ene-3,17-dione

A solution of 23.1 g of 11β-fluoro-7α-(5-tert-butyl-dimethylsilyloxypentyl)oestr-4-ene-3,17-dione in 115 ml of THF and 64 ml of water are stirred at 50° C. for 2.5 h with 128 ml of glacial acetic acid. The reaction mixture is concentrated in vacuo, taken up in ethyl acetate, and the solution is washed with water and dried. 20.4 g of 11β-fluoro-7α-(5-hydroxypentyl)oestr-4-ene-3,17-dione are obtained as a foam.

f) 7α-(5-Bromopentyl)-11β-fluorooestr-4-ene-3,17-dione

A solution of 33 g of 11β-fluoro-7α-(5-hydroxypentyl) oestr-4-ene-3,17-dione in 330 ml of dichloromethane is treated with 28.9 g of triphenylphosphine and 36.7 g of carbon tetrabromide at −5° C. and stirred for 0.5 hours. Dichloromethane is then added and the mixture is washed with water, saturated sodium hydrogencarbonate solution and sodium chloride solution. The organic phase is dried over sodium sulphate and concentrated in vacuo. The crude product is then chromatographed on silica gel using a hexane-ethyl acetate gradient. 28.5 g of 7α-(5-bromopentyl)-11β-fluorooestr-4-ene-3,17-dione of melting point 75–76° C. are obtained.

g) 7α-(5-Bromopentyl)-11β-fluoro-3-hydroxyestra-1,3,5 (10)-trien-17-one 17.0 g of copper(II) bromide are added at 80° C. to 27.8 g of 7α-(5-bromopentyl)-11β-fluorooestr-4-ene-3,17-dione in 190 ml of acetonitrile. After 8 hours, the reaction mixture is stirred into water, extracted 3 times with ethyl acetate, washed twice with ammonium chloride, with sodium hydrogencarbonate and sodium chloride, dried and concentrated in vacuo. After chromatographing the crude product on silica gel using a hexane-ethyl acetate gradient, 20.4 g of 7α-(5-bromo-pentyl)-11β-fluoro-3-hydroxyestra-1,3,5(10)-trien-17-one are obtained as colourless crystals of melting point 178° C.

h) 7α-(5-Bromopentyl)-11β-fluorooestra-1,3,5(10)-triene-3,17β-diol

A solution of 16.2 g of 7α-(5-bromopentyl)-11β-fluoro-3-hydroxyestra-1,3,5(10)-trien-17-one in 162 ml of tetrahydrofuran, and 90 ml of ethanol and 36 ml of water is treated in portions with 4.7 g of sodium borohydride at 0° C. and stirred at 0° C. for 2 hours. It is then added to water, extracted 4 times with ethyl acetate, washed with water and sodium chloride solution, dried over sodium sulphate and concentrated in vacuo. 17.1 g of crude product are obtained. After chromatography on silica gel using hexane/ethyl acetate, 15.6 g of pure 7α-(5-bromopentyl)-11β-fluorooestra-1,3,5(10)-triene-3,17β-diol are obtained.

i) 11β-Fluoro-7α-[5-(methylamino)$_p$entyl]oestra-1,3,5(10)-triene-3,17β-diol

A solution of 2 g of 7α-(5-bromopentyl)-11β-fluorooestra-1,3,5(10)-triene-3,17β-diol in 20 ml of dimethylformamide is stirred at 80° C. for 3.5 hours with 8 ml of a 40% strength aqueous methylamine solution. It is then added to water, extracted 3 times with ethyl acetate, washed with water and sodium chloride solution, dried over sodium sulphate and concentrated in vacuo. 1.77 g of 11β-fluoro-7 (x-[5-(methylamino)-pentyl]oestra-1,3,5(10)-triene-3,17β-diol are obtained.

j) 11β-Fluoro-7α-{5-[methyl-(8,8,9,9,9-pentafluoro-nonyl) aminol pentyl}oestra-1,3,5(10)-triene-3,17β-diol A solution of 1.77 g of 11β-fluoro-7x-[5-(methylamino)-pentyl]oestra-1,3,5(10)-triene-3,17β-diol in 18 ml of dimethylformamide is stirred at a bath temperature of 80° C. for 1 hour with 1.4 g of 8,8,9,9,9-penta-fluorononyl tosylate. The mixture is then added to water, extracted 3 times with ethyl acetate, washed with water and sodium chloride solution, dried over sodium sulphate, concentrated in vacuo and the residue is chromatographed on silica gel using dichloromethane/methanol. 11β-Fluoro-7α-{5-[methyl(8,8, 9,9,9-penta-fluorononyl)amino]pentyl}oestra-1,3,5(10)-triene-3,17β-diol is obtained as crystals of melting point 11° C.

Preparation of the starting compounds:

8,8,9,9,9-Pentafluorononyl Tosylate a) 4-Benzyloxybutan-1-ol 42 a of sodium hydride (60% strength) are introduced in portions into 900 ml of abs. DMF at room temperature. 88.6 ml of 1,4-butanediol in 450 ml of abs. DMF are added dropwise to the suspension cooled to −20° C. such that the internal temperature does not exceed −15° C. After addition is complete, a solution of 121 ml of benzyl bromide in 870 ml of abs. DMF is rapidly added dropwise and the reaction mixture is then stirred at room temperature for 30 minutes. The reaction is ended by careful addition of 315 ml of water. For work-up, the reaction mixture is stirred into 1.5 l of water and extracted 3 times with 1 l of ether in each case. The ethereal phases are combined, washed with water, dried over magnesium sulphate and concentrated in vacuo. Chromatography on silica gel using a hexane-ethyl acetate gradient yields 105 g of 4-benzyloxybutan-1-ol as an oil.

b) 4-Benzyloxy-1-bromobutane 239 g of tetrabromomethane are added in portions to the solution of 105 g of 4-benzyloxybutan-1-ol and 191 g of triphenylphosphine in 1 l of methylene chloride cooled to −15° C. and the mixture is stirred at 0° C. for 1 h after addition is complete. After the reaction mixture has been concentrated in vacuo, purification is carried out by chromatography on silica gel using a hexane-ethyl acetate gradient. 133 g of 4-benzyloxy-1-bromobutane are obtained as an oil.

c) 1-Benzyloxy-8,8,9,9,9-pentafluorononane

10% of a solution of 20 g of 4-benzyloxy-1-bromobutane in 20 ml of abs. THF are first added at room temperature to a suspension of 2.23 g of magnesium turnings in 58 ml of abs. THF. After starting the reaction, which can be achieved by addition of iodine, the remaining solution is added dropwise such that the internal temperature is maintained at 40° C. After addition is complete, the solution is stirred at room temperature for a further hour before it is decanted off from the excess magnesium and transferred to a dropping funnel. This solution is then simultaneously added dropwise at 0° C. with a solution of 21 g of 1,1,1,2,2-pentafluoro-5- iodopentane in 97 ml of abs. THF to a solution of 555 mg of copper(II) chloride and 350 mg of lithium chloride in 58 ml of abs. THF. The reaction mixture is stirred at room temperature for a further hour, then stirred into saturated ammonium chloride solution, extracted 3 times with ether, and the organic phase is dried over magnesium sulphate and concentrated in vacuo. Preparative column chromatography on silica gel using a hexane-ethyl acetate gradient yields 22 g of largely purified 1-benzyloxy-8,8,9,9,9-pentafluorononane as an oil.

d) 8,8,9,9,9-Pentafluorononan-1-ol 16 g of 1-benzyloxy-8,8,9,9,9-pentafluorononane are dissolved in 700 ml of abs. methylene chloride, treated at 0° C. with 18.4 ml of N,N-dimethylaniline and stirred for 5 minutes. 26.4 g of aluminium trichloride are then added in portions and the reaction mixture is warmed to 50° C. for 45 minutes. For work-up, the mixture is allowed to come to room temperature, stirred into 2N hydrochloric acid, extracted 3 times with methylene chloride, dried over magnesium sulphate and concentrated in vacuo. The crude product is chromato-graphed on silica gel using a hexane-ethyl acetate gradient. 8.6 g of 8,8,9,9,9-pentafluorononan-1-ol are obtained as an oil.

e) 8,8,9,9,9-Pentafluorononyl Tosylate 3.0 g of 8,8,9,9,9-pentafluorononan-1-ol are dissolved in 26 ml of abs. pyridine, 3.1 g of p-toluenesulphonyl chloride are added at 0° C. and the mixture is stirred in the cold for 1.5 hours. The reaction mixture is then added to water, extracted 3 times with ether, dried over magnesium sulphate and concentrated in vacuo. Preparative column chromatography on silica gel using a hexane-ethyl acetate gradient leads to 4.1 g of 8,8,9,9,9-pentafluorononyl tosylate as a clear oil.

9,9,10,10,10-Pentafluorodecyl Tosylate a) 5-Benzyloxypentan-1-ol 31.5 g of sodium hydride (60% strength) are ire educed into 900 ml of abs. DMF in portions at room temperature. 104.8 ml of 1,5-pentanediol in 450 ml of abs. DMF are added dropwise to the suspension cooled to −20° C., such that the internal temperature does not exceed −15° C. After addition is complete, a solution of 121 ml of benzyl bromide in 870 ml of abs. DMF is rapidly added dropwise and the reaction mixture is then stirred at room temperature for 30 minutes. The reaction is ended by careful addition of 315 ml of water. For work-up, the reaction mixture is stirred into 1.5 l of water and extracted 3 times with 1 l of ether in each case. The ethereal phases are combined, washed with water, dried over magnesium sulphate and concentrated in vacuo. Chromatography on silica gel using a hexane-ethyl acetate gradient yields 85 g of 5-benzyloxypentan-1-ol as an oil.

b) 5-Benzyloxy-1-bromopentane 179 g of tetrabromomethane are added in portions to the solution of 85 g of 5-benzyloxypentan-1-ol and 143 g of triphenylphosphine in 70 ml of methylene chloride cooled to −15° C. and the mixture is stirred at 0° C. for 3 h after addition is complete. After the reaction mixture has been concentrated in vacuo, purification is carried out by chromatography on silica gel using a hexane-methylene chloride gradient. 71 g of 5-benzyl-oxy-1-bromopentane are obtained as an oil.

c) 1-Benzyloxy-9,9,10,10,10-pentafluorodecane

10% of a solution of 21.1 g of 5-benzyloxy-1-bromopentane in 20 ml of abs. THF are first added at room temperature to a suspension of 2.23 g of magnesium turnings in 58 ml of abs. THF. After starting the reaction, which can be achieved by addition of iodine, the remaining solution is added dropwise such that the internal temperature is maintained at 40° C. After addition is complete, the mixture is stirred at room temperature for a further hour before excess magnesium is decanted off and the solution is transferred to a dropping funnel. This solution is then added dropwise at 0° C. simultaneously with a solution of 21 g of 1,1,1,2,2-pentafluoro-5-iodopentane in 97 ml of abs. THF to a solution of 555 mg of copper(II) chloride and 350 mg of lithium chloride in 58 ml of abs. THF. The reaction mixture is stirred at room temperature for a further hour, then stirred into saturated ammonium chloride solution, extracted 3 times with ether, and the organic phase is dried over magnesium sulphate and concentrated in vacuo. 26.8 g of crude product are obtained, which is employed in the next stage without further purification.

d) 9,9,10,10,10-Pentafluorodecan-1-ol 26 g of 1-benzyloxy-9,9,10,10,10-pentafluorodecane are dissolved in 1000 ml of abs. methylene chloride, treated at 0° C. with 28.9 ml of N,N-dimethylaniline and stirred for 5 minutes. 41.1 g of aluminium trichloride are then added in portions and the reaction mixture is warmed to 50° C. for 45 minutes. For work-up, the mixture is allowed to come to room temperature, stirred into 2N hydrochloric acid, extracted 3 times with methylene chloride, and the organic phase is washed with sodium chloride solution, dried over magnesium sulphate and concentrated in vacuo. The crude product is chromato-graphed on silica gel using a hexane-ethyl acetate radient. 7.8 g of 9,9,10,10,10-pentafluorodecan-1-ol are obtained as an oil.

e) 9,9,10,10,10-Pentafluorodecyl Tosylate 1.0 g of 9,9,10,10,10-pentafluorodecan-1-ol is dissolved in 8 ml of abs. pyridine, 985 mg of p-toluenesulphonyl chloride are added at 0° C. and the mixture is stirred in the cold for 2 hours. The reaction mixture is then added to water, extracted 3 times with ether, dried over magnesium sulphate and concentrated in vacuo. Preparative column chromatography on silica gel using a hexane-ethyl acetate gradient leads to 1.5 g of 9,9,10,10,10-penta-fluorodecyl tosylate as an oil.

N-Methyl-[3(4,4,5,5,5-pentafluoro-pentylthio) propyl]amine a) 3-Iodopropyl-4,4,5,5,5-pentafluoropentyl Sulphide A solution of 22.8 g of 3-chloropropyl-4,4,5,5,5-pentafluoropentyl sulphide in 500 ml of ethyl methyl ketone is stirred under nitrogen at a bath temperature of 100° C. for 5 hours with 40 g of sodium iodide. It is then concentrated to dryness in vacuo, the residue is added to water, and the mixture is extracted three times with ethyl acetate, washed until neutral, and dried over sodium sulphate and concentrated in vacuo. 30.6 g of 3-iodopropyl-4,4,5,5,5-pentafluoropentyl sulphide are obtained.

b) N-Methyl-[3-(4,4,5,5,5-pentafluoropentylthio)-propyl] amine 45 g of methylamine are condensed at a bath temperature of −78° C. into a solution of 30.6 g of 3-iodopropyl-4,4,5, 5,5-pentafluoropentyl sulphide in 200 ml of abs. tetrahydrofuran and the mixture is stirred at room temperature for 1.5 hours and at 60° C. for 4 hours in a pressure reactor. To open the reactor, it is allowed to cool overnight to room temperature and then to −78° C. It is then allowed to come to room temperature, excess methylamine is evaporated, the mixture is diluted with ethyl acetate, washed until neutral, dried over sodium sulphate and concentrated in vacuo, and the residue is chromatographed on silica gel using dichloromethane/methanol. 15.7 g of N-methyl-[3-(4,4,5,5,5-pentafluoropentylthio)propyl]amine are obtained as an oil.

N-Methyl-[3-(4,4,5,5,5-pentafluoro-pentanesulphonyl)propyl]amine a) 3-Chloropropyl-4,4,5,5,5-pentafluoropentane Sulphone A solution of 23 g of 3-chloropropyl-4,4,5,5,5-pentafluoropentyl sulphide in 230 ml of chloroform is treated in portions at 0° C. with 41.8 g of 70% strength m-chloroperbenzoic acid and stirred at room temperature for 1.5 hours. It is then diluted with dichloromethane, washed with sodium hydrogensulphite, sodium hydrogen-carbonate and sodium chloride solution, dried over sodium sulphate and concentrated in vacuo. 23.8 g of pure 3-chloropropyl-4,4,5,5,5-pentafluoropentane sulphone are obtained as crystals of melting point 74–76° C.

b) 3-Iodopropyl-4,4,5,5,5-pentafluoropentane Sulphone

A solution of 23.5 g of 3-chloropropyl-4,4,5,5,5-pentafluoropentane sulphone in 500 ml of ethyl methyl ketone is stirred under nitrogen at a bath temperature of 100° C. for 5 hours with 40 g of sodium iodide. It is then concentrated to dryness in vacuo, added to water, extracted three times with ethyl acetate, washed until neutral, and dried over sodium sulphate and concentrated in vacuo. 30.6 g of 3-iodopropyl-4,4,5,5,5-pentafluoropentane sulphone are obtained as crystals of melting point 88–89° C.

c) N-Methyl-[3-(4,4,5,5,5-pentafluoropentane Sulphonyl) propyl]amine 44 g of methylamine are condensed at a bath temperature of −78° C. into a solution of 23.5 g of 3-iodopropyl-4,4,5,5,5-pentafluoropentane sulphone in 200 ml of abs. tetrahydrofuran and the mixture is stirred at room temperature for 1.5 hours and at 60° C. for 4 hours in a pressure reactor. To open the reactor, it is allowed to cool to room temperature overnight and then to −78° C. It is then allowed to come to room temperature, excess methylamine is evaporated, the mixture is diluted with ethyl acetate, washed until neutral, dried over sodium sulphate and concentrated in vacuo and the residue is chromatographed on silica gel using dichloromethane/ methanol. 14.8 g of N-methyl-[3-(4,4,5,5,5-pentafluoro-pentane sulphonyl)propyl]amine are obtained as crystals of melting point 55–57° C.

1-Bromo-5-tert-butyldimethylsilyloxypentane a) 5-Bromo-1-pentanol 50 ml of concentrated sulphuric acid are added dropwise to a solution of 50 g of 5-bromopentyl acetate in 1.6 l or methanol and the mixture is stirred at room temperature for 30 hours. The methanol is stripped off in vacuo, the residue is taken up in diethyl ether, and the mixture is washed with saturated sodium chloride solution until neutral, dried over sodium sulphate and concentrated. 28 g of 5-bromo-1-pentanol are obtained as a crude product.

b) 1-Bromo-5-tert-butyldimethylsilyloxypentane

A solution of 28 g of the crude 5-bromo-1-pentanol in 144 ml of tetrahydrofuran is treated with 24 g of imidazole. A solution of 30.3 g of tert-butyldimethyl-chlorosilane in 46 ml of tetrahydrofuran is then added dropwise and the mixture is stirred at room temperature for 4 hours. The reaction mixture is poured into water, extracted by shaking with diethyl ether, and the organic phase is washed 4 times with water, dried over sodium sulphate and concentrated. The crude product is chromatographed on silica gel using hexane/diethyl ether. 42 g of the title compound are obtained as a colourless liquid.

EXAMPLE 5

11β-Fluoro-7α-{5-[methyl-nonyl-amino]pentyl}-oestra-1,3,5(10)-triene-3,17β-diol a) 7α-(5-Chloropentyl)-11β-fluorooestr-4-ene-3,17-dione 20% of a solution of 39 ml of 1-bromo-5-chloropentane in 300 ml of THF are first added under nitrogen to a suspension of 7.2 g of magnesium turnings in 100 ml of THF. After starting the reaction, which can be achieved by addition of iodine and dibromomethane, the remaining solution is added dropwise such that the internal temperature does not exceed 35° C. In a second flask, 51.2 g of lithium bromide are added to a suspension of 28.1 g of copper(I) iodide in 130 ml of THF at 0° C., the internal temperature rising to 40° C. 49.4 ml of 1,3-dimethyl-3,4,5,6-tetrahydro-(1H)-pyrimidin-2-one are then added without cooling and the mixture is stirred at 40° C. for 15 minutes. A clear solution is obtained, which is added dropwise to the Grignard solution cooled to −50° C. The mixture is then stirred at −30° C. for 15 minutes and treated dropwise at −70° C. with a solution of 25 g of 11β-fluorooestra-4,6-diene-3,17-dione in 260 ml of THF, 26 ml of 1,3-dimethyl-3,4,5,6-tetra-hydro-(1H)-pyrimidin-2-one and 59 ml of trimethyl-chlorosilane such that the internal temperature does not exceed −65° C. The mixture is stirred in the cold for 30 minutes, then 34.7 ml of glacial acetic acid are added dropwise, the cooling bath is removed and stirring is then continued at room temperature for 1 hour. For work-up, the reaction mixture is added to 1.5 l of water, diluted with the same amount of ethyl acetate, the precipitate is filtered off through Celite, then washed with ethyl acetate, and the aqueous phase is extracted 3 times with ethyl acetate, washed with sodium hydrogencarbonate and sodium chloride solution, dried over magnesium sulphate and concentrated in vacuo. After chromatographing the crude product on silica gel using a hexane-ethyl acetate gradient, 22.1 g of 7α-(5-chloropentyl)-11β-fluorooestr-4-ene-3,17-dione are obtained.

b) 7α-(5-Chloropentyl)-11β-fluoro-3-hydroxyestra-1,3,5(10)-trien-17-one 25.4 g of copper(II) bromide and 4.9 g of lithium bromide in 95 ml of anhydrous acetonitrile are added at 80° C. to 22.1 g of 7α-(5-chloropentyl)-11β-fluorooestr-4-ene-3,17-dione in 160 ml of anhydrous acetonitrile. After 20 minutes, the reaction mixture is cooled to 0° C. and 200 ml of saturated sodium hydrogencarbonate solution are added dropwise. The solution is then stirred into 750 ml of water, brought to pH=6 with 2N hydrochloric acid, extracted 3 times with ethyl acetate, washed with sodium chloride solution, dried over magnesium sulphate and concentrated in vacuo. Chromatography of the crude produre o silica gel using a hexane-ethyl acetate gradient yields 14.7 g of 7α-(5-chloropentyl)-11β-fluoro-3-hydroxyestra-1,3,5(10)-trien-17-one.

c) 11β-Fluoro-3-hydroxy-7α-(5-iodopentyl)oestra-1,3,5-(10)trien-7-one 5.0 g of 7α-(5-chloropentyl)-11β-fluoro-3-hydroxyestra-1,3,5(10)trien-17-one are dissolved in 80 ml of ethyl methyl ketone, treated with 5.7 g of sodium iodide and stirred overnight at a bath temperature of 90° C. For work-up, the reaction mixture is cooled to room temperature, stirred into water, extracted 3 times with ethyl acetate, washed with sodium chloride solution, dried over magnesium sulphate and concentrated in vacuo. 6.8 g of 11β-fluoro-3-hydroxy-7α-(5-iodopentyl)-oestra-1,3,5(10)-trien-17-one are obtained as a crude product, which is employed in the next stage without further purification.

c) 11β-Fluoro-3-hydroxy-7α-[5-(methylamino)pentyl]-oestra-1,3,5(10)-trien-17-one 5.1 g of methylamine are condensed at −78° C. into a solution of 6.8 g of 11β-fluoro-3-hydroxy-7(x-(5-iodopentyl)oestra-1,3,5(10)-trien-17-one in 35 ml of anhydrous tetrahydrofuran and the mixture is stirred overnight at room temperature in a pressure reactor. After the pressure reactor has been opened at −20° C., the mixture is allowed to come to room temperature in order to allow excess methylamine to evaporate. The reaction solution is then added to saturated sodium hydrogencarbonate solution, extracted 3 times with ethyl acetate, dried over magnesium sulphate and concentrated in vacuo. 6.7 g of 11β-fluoro-3-hydroxy-7α-[5-(methylamino)pentyl]oestra-1,3,5(10)-trien-17-one are obtained as crude product.

d) 11β-Fluoro-3-hydroxy-7α-(5-[methyl-nonyl-amino]-pentyl)oestra-1,3,5(10)-trien-17-one 526 mg of 11β-fluoro-3-hydroxy-7α-[5-(methylamino)-pentyl]oestra-1,3,5(10)-trien-17-one and 127 mg of iodononane are dissolved in 5 ml of anhydrous DMF and stirred at a bath temperature of 100° C. for 4 h. For work-up, the mixture is added to half-saturated sodium hydrogencarbonate solution, extracted 3 times with methylene chloride, dried over magnesium sulphate and concentrated in vacuo. Preparative column chromatography yields 85 mg of 11β-fluoro-3-hydroxy-7α-{5-[methyl-nonyl-amino]pentyl}oestra-1,3,5(10)-trien-17-one as a foam.

e) 11β-Fluoro-7α-{5-(methyl-nonyl-amino]pentyl}-oestra-1,3,5(10)-triene-3,17β-diol 85 mg of 11β-fluoro-3-hydroxy-7α-{5-[methyl-nonyl-amino]pentyl}oestra-1,3,5(10)-trien-17-one are dissolved in 3 ml of methanol and treated with 25 mg of sodium borohydride. After stirring at room temperature for 30 minutes, the solvent is for the most part stripped off in vacuo, the residue is treated with sodium chloride solution, and the mixture is extracted 3 times with methylene chloride, dried over magnesium sulphate and concentrated in vacuo. Preparative thin-layer chromatography using methylene chloride/methanol=9/1+0.5% triethylamine as a mobile phase leads to 33 mg of 11β-fluoro-7α-{5-[methyl-nonyl-amino]pentyl}-oestra-1,3,5(10)-triene-3,17β-diol as a foam.

EXAMPLE 6

11β-Fluoro-7α-{6-[methyl-(8,8,9,9,9-pentafluorononyl)-amino]hexyl}oestra-1,3,5(10)-triene-3, 17-diol a) 7α-(6-Chlorohexyl)-11β-fluorooestr-4-ene-3,17-dione 30 ml of a solution of 41 ml of 1-bromo-6-chlorohexane in 270 ml of THF are first added under nitrogen to a suspension of 6.8 g of magnesium turnings in 100 ml of THF. After starting the reaction, the remaining solution is added dropwise such that the internal temperature does not exceed 35° C. In a second flask, 48.1 g of lithium bromide are added to a suspension of 4 g of copper(I) iodide in 120 ml of THF at 0° C., the internal temperature rising to 40° C. 46.4 ml of 1,3-dimethyl-3,4,5,6-tetrahydro-(1H)-pyrimidin-2-one are then added without cooling and the mixture is stirred at 40° C. for 30 minutes. A clear solution is obtained, which is added dropwise to the Grignard solution cooled to −40° C. The mixture is then stirred at −30° C. for 30 minutes and treated dropwise at −50° C. with a solution of 23.5 g of 11β-fluorooestra-4,6-diene-3,17-dione in 230 ml of THF, 24.6 ml of 1,3-dimethyl-3,4,5,6-tetrahydro-(1H)-pyrimidin-2-one and 55 ml of trimethylchlorosilane such that the internal temperature does not exceed −40° C. The mixture is stirred in the cold for 1 h, then 32 ml of glacial acetic acid are added dropwise, the cooling bath is removed and the mixture is stirred at room temperature for 1 hour. For work-up, the reaction mixture is added to 1.5 l of water, diluted with the same amount of ethyl acetate, the precipitate is removed by means of Celite, washed with ethyl acetate, and the aqueous phase is extracted 3 times with ethyl acetate, washed with sodium hydrogencarbonate and sodium chloride solution, dried over magnesium sulphate and concentrated in vacuo. After chromatographing the crude product on silica gel using a hexane-ethyl acetate gradient, 25.2 g of 7α-(6-chlorohexyl)-11β-fluorooestr-4-ene-3,17-dione are obtained.

b) 7α-(6-Chlorohexyl-11β-fluoro-3-hydroxyestra-1,3,5(10)-trien-17-one 28.1 g of copper(II) bromide and 5.4 g of lithium bromide in 105 ml of anhydrous acetonitrile are added at 80° C. to 25.2 g of 7α-(6-chlorohexyl)-11β-fluorooestr-4-ene-3,17-dione in 175 ml of anhydrous acetonitrile. After 15 minutes, the reaction mixture is cooled to 0° C. and 250 ml of saturated sodium hydrogencarbonate solution are added dropwise. The solution is then stirred into 1 litre of water, brought to pH=6 with 2N hydrochloric acid, extracted 3 times with ethyl acetate, washed with sodium chloride solution, dried over magnesium sulphate and concentrated in vacuo. Chromatography of the crude product on silica gel using a hexane-ethyl acetate gradient yields 5.7 g of 7α-(6-chlorohexyl)-11β-fluoro-3-hydroxyestra-1,3,5(10)-trien-17-one as a foam.

c) 11β-Fluoro-3-hydroxy-7α-(6-iodohexyl)oestra-1,3,5(10)-trien-17-one 2.7 g of 7α-(6-chlorohexyl)-11β-fluoro-3-hydroxyestra-1,3,5(10)-trien-17-one are dissolved in 40 ml of ethyl methyl ketone, treated with 3.0 g of sodium iodide and stirred overnight at a bath temperature of 90° C. For work-up, the reaction mixture is cooled to room temperature, stirred into water, extracted 3 times with ethyl acetate, washed with sodium chloride solution, dried over magnesium sulphate and concentrated in vacuo. 3.4 g of 11β-fluoro-3-hydroxy-7α-(6-iodo-hexyl)oestra-1,3,5(10)-trien-17-one are obtained as a crude product which is employed in the next stage without further purification.

d) 11β-Fluoro-3-hydroxy-7α-[6-(methylamino)hexyl]-oestra-1,3,5(10)trien-17-one 718 mg of methylamine are condensed at −78° C. into a solution of 960 mg of 11β-fluoro-3-hydroxy-7α-(6-iodo-hexyl)oestra-1,3,5(10)-trien-17-one in 9 ml of anhydrous tetrahydrofuran and the mixture is stirred overnight at room temperature in a pressure reactor. After the pressure reactor has been opened at −20° C., it is allowed to come to room temperature in order to allow excess methylamine to evaporate. The reaction solution is then added to saturated sodium hydrogencarbonate solution, extracted 3 times with ethyl acetate, dried over sodium sulphate and concentrated in vacuo. 763 mg of 11β-fluoro-3-hydroxy-7α-[5-(methylamino)hexyl]oestra-1,3,5(10)-trien-17-one are obtained as a crude product.

e) 11β-Fluoro-3-hydroxy-7α-{6-[methyl-(8,8,9,9,9-pentafluorononyl)amino]hexyl}oestra-1,3,5(10)-trien-17-one A solution of 381 mg of 11β-fluoro-3-hydroxy-7α-[6-(methylamino)hexyl]oestra-1,3,5(10)-trien-17-one in 5 ml of dimethylformamide is stirred at a bath temperature of 100° C. for 2 hours with 200 mg of 8,8,9,9,9-pentafluorononyl tosylate. It is then added to half-saturated sodium hydrogencarbonate solution, extracted three times with methylene chloride, dried over magnesium sulphate, concentrated in vacuo and chromatographed on silica gel using dichloromethane/methanol. 90 mg of 11β-fluoro-3-hydroxy-7α-{6-[methyl-(8,8,9,9,9-pentafluorononyl)-amino]hexyl}oestra-1,3,5(10)-trien-17-one are obtained as a foam.

f) 11β-Fluoro-7α-{6-[methyl-(8,8,9,9,9-pentafluoro-nonyl)amino]hexyl}oestra-1,3,5(10)-triene-3,17β-diol 89 mg of 11β-fluoro-3-hydroxy-7α-{6-[methyl-(8,8,9,9,9-pentafluorononyl)amino]hexyl}oestra-1,3,5(10)-trien-17-one are dissolved in 2 ml of ethanol and treated with 22 mg of sodium borohydride. After stirring at room temperature for 1 hour, the solvent is for the most part stripped off in vacuo, the residue is treated with sodium chloride solution, and the mixture is extracted 3 times with methylene chloride, dried over magnesium sulphate and concentrated in vacuo. Preparative thin-layer chromatography using methylene chloride/methanol=9/1 as an eluent leads to 53 mg of 11β-fluoro-7x-{5-[methyl-(8,8,9,9,9-pentafluorononyl)amino]hexyl}oestra-1,3,5(10)-triene-3,17β-diol are obtained as a foam, $[\alpha]_D = +32°$ (c=1.0 in chloroform).

EXAMPLE 7

11β-Fluoro-7α-{5-[methyl-(7,7,8,8,9,9,10,10,10-nonafluorodecyl)amino]pentyl}oestra-1,3,5(10)-triene-3,17β-diol A solution of 466 mg of 7α-(5-bromopentyl)-11β-fluorooestra-1,3,5(10)-triene-3,17-diol in 10 ml of 1-methyl-2-pyrrolidinone is stirred at a bath temperature of 80° C. for 3 hours with 1.0 g of methyl-(7,7,8,8,9,9,10,10,10-nonafluorodecyl)amine. For work-up, the mixture is added to saturated sodium chloride solution, extracted with ether, dried over sodium sulphate, concentrated in vacuo and the residue is chromatographed on silica gel using ethyl acetate/methanol. 546 mg of 11β-fluoro-7α-{5-[methyl-(7,7,8,8,9,9,10,10,10-nonafluorodecyl)amino]pentyl}-oestra-1,3,5(10)triene-3, 17β-diol are obtained as a foam, $[\alpha]_D = +39°$ (c=0.5 in $CHCl_3$)

EXAMPLE 8

11β-Fluoro-7α-{5-[(3,4,4,5,5,5-hexafluoropent-2-enyl)-methylamino]pentyl}oestra-1,3,5(10)-triene-3,17β-diol a) 11β-Fluoro-7α-{5-[(3,4,4,5,5,5-hexafluoropent-2-enyl)methylamio]pentyl}-3-hydroxyestra-1,3,5(10)-trien-17-one 880 mg of 11β-fluoro-3-hydroxy-7α-(5-iodopentyl)oestra-1,3,5(10)-trien-17-one and 1.26 g of (3,4,4,5,5,5-hexa-fluoropent-2-enyl)methylamine are dissolved in 20 ml of N-methylpyrrolidone and stirred at a bath temperature of 80° C. for 3 hours. After the reaction solution has cooled to room temperature, the mixture is added to saturated sodium chloride solution, extracted with diethyl ether, dried and concentrated in vacuo. 1.86 g of 11β-fluoro-7α-{5-[(3,4,4,5,5,5-hexafluoropent-2-enyl)methylamino]pentyl}-3-hydroxyestra-1,3,5(10)-trien-17-one are obtained as a crude product which is employed in the next stage without purification.

b) 11β-Fluoro-7α-{5-[(3,4,4,5,5,5-hexafluoropent-2-enyl) methylamino]pentyl}oestra-1,3,5(10)-triene-3,17β-diol 1.86 g of 11β-fluoro-7α-{5-[(3,4,4,5,5,5-hexafluoropent-2-enyl)methylamino]pentyl}-3-hydroxyestra-1,3,5(10)-trien-17-one are dissolved in 15 ml of methanol and cautiously treated with 222 mg of sodium borohydride. After stirring at room temperature for 15 minutes, the mixture is added to saturated sodium chloride solution, extracted with methylene chloride, dried over magnesium sulphate and concentrated in vacuo. After chromatographing the crude product on silica gel using a hexane-ethyl acetate and an ethyl acetate-acetone gradient, 241 mg of 11β-fluoro-7α-{5-[(3,4,4,5,5,5-hexafluoropent-2-enyl)methyl-amino]pentyl}oestra-1,3,5(10)-triene-3,17β-diol of melting point 122° C. are obtained, $[\alpha]_D = +47°$ (c=0.5 in $CHCl_3$)

EXAMPLE 9

11β-Fluoro-7α-{5-[N-methyl-N-3-(4,4,5,5,5-pentafluoro-pentyloxy)propylamino]pentyl}oestra-1,3,5(10)-triene-3,17β-diol a) 11β-Fluoro-7α-(5-bromopentyl)-3-(tetrahydropyran-2-yloxy)oestra-1,3,5(10)-trien-17-one 8.4 g of 11β-fluoro-7α-(5-bromopentyl)-3-hydroxyestra-1,3,5(10)-trien-17-one in 90 ml of tetrahydrofuran are allowed to react at room temperature with 9.0 ml of 3,4-dihydropyran and 805 mg of p-toluenesulphonic acid hydrate. After 7 h, 1 ml of triethylamine is added, and the mixture is diluted with ethyl acetate, washed with saturated sodium chloride solution until neutral and dried over sodium sulphate. Chromatography on silica gel using a hexane-ethyl acetate gradient affords 7.6 g of 11β-fluoro-7α-(5-bromopentyl)-3-(tetrahydropyran-2-yloxy)oestra-1,3,5(10)-trien-17-one as a foam.

b) 11β-Fluoro-7α-{5-[(3-tert-butyldimethylsilyloxy-propyl)methylamino]pentyl}-3-tetrahydropyran-2-yloxy)oestra-1,3,5(10)-trien-17-one 6.0 g of 11β-fluoro-7α-(5-bromopentyl)-3-(tetrahydro-pyran-2-yloxy)oestra-1,3,5(10)-trien-17-one in 130 ml of dimethylformamide are reacted at 100° C. with 5.7 g of 1-N-methylamino-3-tert-butyldimethylsilyloxypropane (prepared from 1-bromo-3-hydroxypropane by reaction with tert-butyldimethylsilyl chloride to give 1-bromo-3-tert-butyldimethylsilyloxypropane and subsequent reaction with methylamine). After 7 hours, the mixture is diluted with ethyl acetate, washed with saturated sodium chloride solution and concentrated in vacuo. After chromatographing the crude product on silica gel using a methylene chloride-methanol gradient, 4.5 g of 11β-fluoro-7α-{5-[(3-tert-butyldimethylsilyloxypropyl)-methylamino]pentyl}-3-tetrahydropyran-2-yloxy)oestra-1,3,5(10)-trien-17-one are obtained as an oil.

c) 11β-Fluoro-7α-{5-[(3-hydroxypropyl)methylamino]-pentyl}oestra-1,3,5(10)-trien-17-one 2.3 g of 11β-fluoro-7α-{5-[(3-tert-butyldimethylsilyl-oxypropyl)methylamino]pentyl}-3-(tetrahydropyran-2-yloxy)oestra-1,3,5(10)-trien-17-one in 23 ml of tetrahydrofuran are reacted at room temperature with 6 ml of tetrabutylammonium fluoride solution (1M in tetrahydrofuran). After 2 hours, the mixture is diluted with ethyl acetate, washed with saturated sodium chloride solution, dried and concentrated in vacuo. Chromatography of the crude product on silica gel using a methylene chloride-methanol gradient affords 1.5 g of 11β-fluoro-7α-{5-[(3-hydroxypropyl)methylamino]-pentyl}oestra-1,3,5(10)-trien-17-one as a foam.

d) 11β-Fluoro-3-(tetrahydropyran-2-yloxy)-7α-{5-[N-methyl-N-3-(4,4,5,5,5-pentafluoropentyloxy)propyl-amino]pentyl}oestra-1,3,5(10)-trien-17-one 1.8 g of pentafluoropentyl iodide, 10 ml of 40% sodium hydroxide solution and 465 mg of tetrabutylammonium hydrogensulphate are added at room temperature to 710 mg of 11β-fluoro-7α-{5-[(3-hydroxypropyl)methyl-amino] pentyl}oestra-1,3,5(10)-trien-17-one in 10 ml of toluene. After 6 days, the reaction mixture is added to ice/water, extracted with ethyl acetate, washed with saturated sodium chloride solution, dried and concentrated in vacuo. After chromatographing the crude product on silica gel using a methylene chloride-methanol gradient, 123 mg of 11β-fluoro-3-(tetrahydropyran-2-yloxy)-7α-{5-[N-methyl-N-3-(4,4,5,5,5-pentafluoropentyloxy)propylamino]pentyl}-oestra-1,3,5(10)-trien-17β-ol are obtained as an oil.

e) 11β-Fluoro-3-(tetrahydropyran-2-yloxy)-7α-{5-[N-methyl-N-3-(4,4,5,5,5-pentafluoropentyloxy)propyl-amino]pentyl}oestra-1,3,5(10)-trien-17β-ol 120 mg of 11β-fluoro-3-(tetrahydropyran-2-yloxy)-7α-{5-[N-methyl-N-3-(4,4,5,5,5-pentafluoropentyloxy)propyl-amino]pentyl}oestra-1,3,5(10)-trien-17-one are reduced at room temperature using 20 mg of sodium borohydride in a mixture of 1 ml of tetrahydrofuran, 0.6 ml of ethanol and 0.3 ml of water. After 1 h, the mixture is diluted with ethyl acetate, washed with water until neutral, concentrated in vacuo and the residue is dried. 76 mg of 11β-fluoro-3-(tetrahydropyran-2-yloxy)-7α-{5-[N-methyl-N-3-(4,4,5,5,5-pentafluoropentyloxy)-propylamino]pentyl}oestra-1,3,5(10)-trien-17β-ol are obtained as a crude product.

f) 11β-Fluoro-7α-{5-[N-methyl-N-3-(4,4,5,5,5-pentafluoropentyloxy)propylamino]pentyl}oestra-1,3,5(10)-triene-3,17β-diol 75 mg of 11β-fluoro-3-(tetrahydropyran-2-yloxy)-7α-{5-[N-methyl-N-3-(4,4,5,5,5-pentafluoropentyloxy)propyl-amino]pentyl}oestra-1,3,5(10)-trien-17β-ol are reacted at room temperature with 50 mg of oxalic acid in 1 ml of methanol and 0.1 ml of water. After 2 hours, the mixture is diluted with methylene chloride, washed with saturated sodium chloride solution until neutral, dried and concentrated in vacuo. After chromatographing on silica gel using a methylene chloride-methanol gradient, the crude product affords 25 mg of 11β-fluoro-7α-{5-[N-methyl-N-3-(4,4,5,5,5-pentafluoro-pentyloxy)propylamino]pentyl}oestra-1,3,5(10)-triene-3,17β-diol as a foam.

EXAMPLE 10

11β-Fluoro-7α-{5-[methyl(2-p-tolylethyl)-amino]pentyl}oestra-1,3,5(10)-triene-3,17β-diol 660 mg of 7α-(5-bromopentyl)-11β-fluorooestra-1,3,5(10)-triene-3,17β-diol are dissolved in 10 ml of N-methylpyrrolidone, treated with 1.2 g of methyl-(2-p-tolylethyl)amine and stirred at a bath temperature of 80° C. for 3 hours. For work-up, the mixture is added to saturated sodium chloride solution, extracted with ethyl acetate, dried over sodium sulphate and concentrated to dryness in vacuo. Column-chromatographic purification on silica gel using an ethyl acetate-methanol-ammonia gradient and subsequent crystallization from ethyl acetate/methylene chloride/hexane yields 277 mg of 11β-fluoro-7α-{5-[methyl-(2-p-tolylethyl)amino]pentyl}oestra-1,3,5(10)-triene-3,17β-diol of melting point 142–143° C.

Preparation of the Starting Compounds:
a) 2-p-Tolylethyl Tosylate 2.8 ml of 2-p-tolylethanol are introduced into 40 ml of pyridine with ice-bath cooling, treated with 4.96 g of p-toluenesulphonyl chloride, and stirred at 0° C. for 30 minutes and at room temperature for 2 hours. The reaction mixture is then slowly stirred into about 150 g of ice/water. The precipitated product is filtered off with suction, washed a number of times with water, dissolved in methylene chloride, dried over magnesium sulphate and concentrated in vacuo. 5.8 g of 2-p-tolylethyl tosylate are obtained, which is employed in the next stage without further purification.

b) Methyl-(2-p-tolylethyl)amine 9.2 g of methylamine are condensed at −20° C. into a solution of 5.8 g of 2-p-tolylethyl tosylate in 15 ml of abs. tetrahydrofuran and the mixture is stirred overnight at room temperature in a pressure vessel. After the pressure vessel has been opened at −20° C., it is allowed to come to room temperature in order to allow excess methylamine to evaporate. The reaction solution is taken up in ether, washed with water and saturated sodium chloride solution, dried over magnesium sulphate and concentrated to dryness in vacuo. 5.39 g of methyl-(2-p-tolylethyl)amine are obtained, which is reacted further as a crude product.

What is claimed is:

1. Combination preparation of an oestrogen and an antioestrogen, characterized in that the oestrogen is selected from the group consisting of 17-β-oestradiol, 17-α-ethynyloestradiol, oestriol, oestrone, oestrone sulphate, oestrogen sulphamates, 17α-oestradiol, mestranol, stilbestrol, esters of 17β-oestradiol, oestradiol valerate and naturally conjugated oestrogens and in that the antioestrogen is a substituted 7α-(ξ-aminoalkyl)oestratriene of the general formula I (I)

in which
the side chain SK is a radical of the subformula where m is 4, 5 or 6,
n is 0, 1 or 2,
x is 0, 1 or 2,
A is a hydrogen atom or a $C_{1-5}$-alkyl group,
B and D are each a hydrogen atom, or
A and B together are an alkylene group —$(CH_2)_p$— with p=2, 3, 4 or 5 and D is a hydrogen atom or
A and D together are an alkylene group —$(CH_2)_q$- with q=2, 3 or 4 and B is a hydrogen atom, and
E is an unsubstituted or mono- to pentafluorinated ethyl radical, or the terminal substituent —$(CH_2)_3$—E in the side chain is replaced by an optionally substituted aryl or heteroaryl radical which is bonded to the sulphur atoms directly or via a mono-, di- or trimethylene group,
$R^3$ is a hydrogen atom, a hydrocarbon radical having up to 8 carbon atoms or a radical of the subformula $R^{3'}$—C(O)—, in which $R^{3'}$ is a hydrogen atom or a hydrocarbon radical having up to 8 carbon atoms or a phenyl radical,
$R^{11}$ is a hydrogen atom, a halogen atom or a nitrooxy group —O—$NO_2$,
$R^{14}$, $R^{15\alpha}$, $R^{15\beta}$, $R^{16\alpha}$ and $R^{16\beta}$ are each a hydrogen atom or
$R^{14}$ and $R^{15\alpha}$ are an additional bond or a methylene bridge, or
$R^{15\beta}$ is a methyl group and $R^{15\alpha}$ is a hydrogen atom, or
$R^{15\alpha}$ and $R^{15\beta}$ are each a methyl group, or
$R^{15\beta}$ and $R^{16\beta}$ together are a methylene bridge, or
$R^{16\alpha}$ or $R^{16\beta}$ is a halogen atom or
$R^{16\alpha}$ and $R^{16\beta}$ together are a methylidene group and the remaining substituents $R^{14}$, $R^{15\alpha}$, $R^{15\beta}$, $R^{16\alpha}$ and $R^{16\beta}$ are each a hydrogen atom, $R^{17'}$ in the α- or β-position is a hydrogen atom, a $C_{1-5}$-alkyl, $C_{2-5}$-alkenyl or $C_{2-5}$-alkynyl group or a trifluoromethyl group and $R^{17''}$ is a hydrogen atom or a radical of the subformula $R^{17'''}$—C(O)—, in which $R^{17'''}$ is a hydrogen atom or a hydrocarbon radical having up to 8 carbon atoms, or, if $R^{17'}$ is located in the α-position, $R^{17'}$ additionally together with $R^{14}$ is an ethanobridge, with the proviso that, if A and B together are not —(CH$_2$)$_p$— or A and D together are not —(CH$_2$)$_q$—, at least one of the substituents $R^{11}$, $R^{14}$, $R^{15\alpha}$, $R^{15\beta}$, $R^{16\alpha}$ and $R^{16\beta}$ is not a hydrogen atom, and their physiologically tolerable addition salts with organic and inorganic acids.

2. Combination preparation according to claim 1, characterized in that the ratio of the dose of the oestrogen to the dose of the antioestrogen is 1:5 to 1:500.

3. Combination preparation according to claim 1, characterized in that the antioestrogen is 11β-fluoro-7α-{5-[N-methyl-N-3-(4,4,5,5,5-pentafluoropentylthio)propylamino]pentyl}oestra-1,3,5(10)-triene-3,17β-diol.

4. A pharmaceutical composition for hormone replacement therapy comprising a combination preparation according to claim 1 and a pharmaceutically acceptable carrier.

5. A composition according to claim 1, wherein the estrogen is estradiol valerate or a naturally conjugated estrogen.

6. A composition according to claim 2, wherein said ratio is 1:20 to 1:200.

7. A composition according to claim 2, wherein said ratio is 1:50 to 1:100.

8. A composition according to claim 2, wherein the estrogen is 17β-estradiol.

9. A pharmaceutical composition, comprising a composition according to claim 1, and a pharmaceutically acceptable carrier.

10. A method for treating dysmenorrhea, dysfunctional uterine haemorrhages, acne, restenosis or arteriosclerosis, comprising administering to a patient in need thereof an effective amount of a composition according to claim 1.

11. The method according to claim 10, wherein the estrogen is administered orally, transdermally, as an implant or intravenously, and the antiestrogen is administered orally, transdeimally, as an implant or intravenously.

12. The method according to claim 10, wherein the antiestrogen does not pass into the central nervous system.

13. A method for treating dysmenorrhea, comprising administering to a patient in need thereof an effective amount of a composition according to claim 1.

14. A method for treating dysfunctional uterine haemorrhages, comprising administering to a patient in need thereof an effective amount of a composition according to claim 1.

15. A method for treating acne, comprising administering to a patient in need thereof an effective amount of a composition according to claim 1.

16. A method for treating restenosis, comprising administering to a patient in need thereof an effective amount of a composition according to claim 1.

17. A method for treating arteriosclerosis, comprising administering to a patient in need thereof an effective amount of a composition according to claim 1.

18. A method for hormone replacement therapy comprising administering to a patient in need thereof an effective amount of a combination preparation according to claim 1.

* * * * *

UNITED STATES PATENT AND TRADEMARK OFFICE
CERTIFICATE OF CORRECTION

PATENT NO.    : 6,677,324 B1
DATED         : January 13, 2004
INVENTOR(S)   : Rudolf Knauthe et al.

It is certified that error appears in the above-identified patent and that said Letters Patent is hereby corrected as shown below:

Column 22,
Line 40, reads "S," should read -- 5 --

Column 23,
Line 22, reads "170-diol," should read -- 17β-diol --

Column 24,
Line 12, reads "transdeimally," should read -- transdermally --

Signed and Sealed this

Seventh Day of September, 2004

JON W. DUDAS
*Director of the United States Patent and Trademark Office*